United States Patent [19]
Yeh

[11] Patent Number: 5,861,127
[45] Date of Patent: Jan. 19, 1999

[54] PORTABLE AIR PURIFYING APPARATUS

[76] Inventor: Kuo Chung Yeh, No. 149, Sec. 3, Lung Kang Road, Chung-Li City, Taiwan

[21] Appl. No.: 911,203

[22] Filed: Jul. 11, 1997

[51] Int. Cl.$^6$ .............................. A62B 29/00; H01T 23/00
[52] U.S. Cl. .......................... 422/121; 422/123; 340/575; 361/232
[58] Field of Search ................................... 422/120, 121, 422/123; 340/575; 361/232

[56] References Cited

U.S. PATENT DOCUMENTS

| | | | |
|---|---|---|---|
| 3,885,576 | 5/1975 | Symmes | 340/407 |
| 4,203,098 | 5/1980 | Muncheryan | 340/575 |
| 4,713,724 | 12/1987 | Voelkel | 361/232 |
| 4,911,737 | 3/1990 | Yehl et al. | 95/81 |
| 5,010,777 | 4/1991 | Yehl et al. | 95/75 |
| 5,043,840 | 8/1991 | Yehl et al. | 361/231 |
| 5,193,048 | 3/1993 | Kaufman et al. | 361/232 |
| 5,667,564 | 9/1997 | Weinberg | 422/120 |

*Primary Examiner*—Krisanne Thornton
*Assistant Examiner*—Fariborz Moazzam
*Attorney, Agent, or Firm*—Bacon & Thomas, PLLC

[57] ABSTRACT

A portable air purifying apparatus including a high frequency voltage booster and an anion generator. The high frequency voltage booster is comprised of a control box accommodating therein a circuit board and two batteries. The circuit board has electronic components assembled thereon to form a high frequency high voltage circuit for generating high frequency high voltage pulse currents when the batteries supply electric currents. The anion generator is comprised of a generator body accommodating therein a discharge electrode, a necklace attached to the generator body, and a terminal connector. The generator body has two air vents. The high frequency voltage booster and the anion generator may be carried around by the user. The terminal connector may be plugged into the terminal socket of the high frequency voltage booster to allow output of high voltage pulse currents so that the discharge electrode inside the generator body may discharge high frequency high voltage currents to generate many anions that may escape through the air vents of the generator body into the air so as to react with and decompose the viruses floating in the air, thereby purifying the air around the user and avoiding viral infections.

3 Claims, 5 Drawing Sheets

PORTABLE AIR PURIFYING APPARATUS

BACKGROUND OF THE INVENTION (a) Field of the Invention

The present invention relates generally to a portable air purifying apparatus, and more particularly to an air purifier that utilizes electronic circuit combinations to generate a high frequency, high voltage pulse current that may harmonize with a discharge electrode of a portable anion generator and may be transmitted back to the anion generator for generating many anions that will react with and decompose viruses in the air, thereby purifying the air surrounding the user.

(b) Description of the Prior Art

In densely populated industrial and commercial sites, pollutants and viruses using air as their medium are everywhere. They are the causes of various infectious diseases, allergy, or chronic diseases.

There have been developed air purifiers for installation in air conditioners to help purify air and kill germs in the air so as to provide fresh indoor air. However, in places like hospitals, stations, and department stores where there are crowds of people, the above-mentioned air purifiers that are fixedly installed are of no use. It is therefore desirable to have a portable air purifier that can purify the surrounding air to ward off viruses and pollutants floating in the air.

SUMMARY OF THE INVENTION

Accordingly, a primary object of the present invention is to provide a portable air purifying apparatus that may be carried around by the user to generate anions for purifying the surrounding air so as to effectively avoid viral infections.

Another object of the present invention is to provide a high frequency voltage booster for generating high frequency high voltage pulse currents that may be output to an anion generator, or an electrode clamp, or a buzzer electric shock head for various purposes including purification of air, drowsiness repression, and self defense.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

Figure 1:
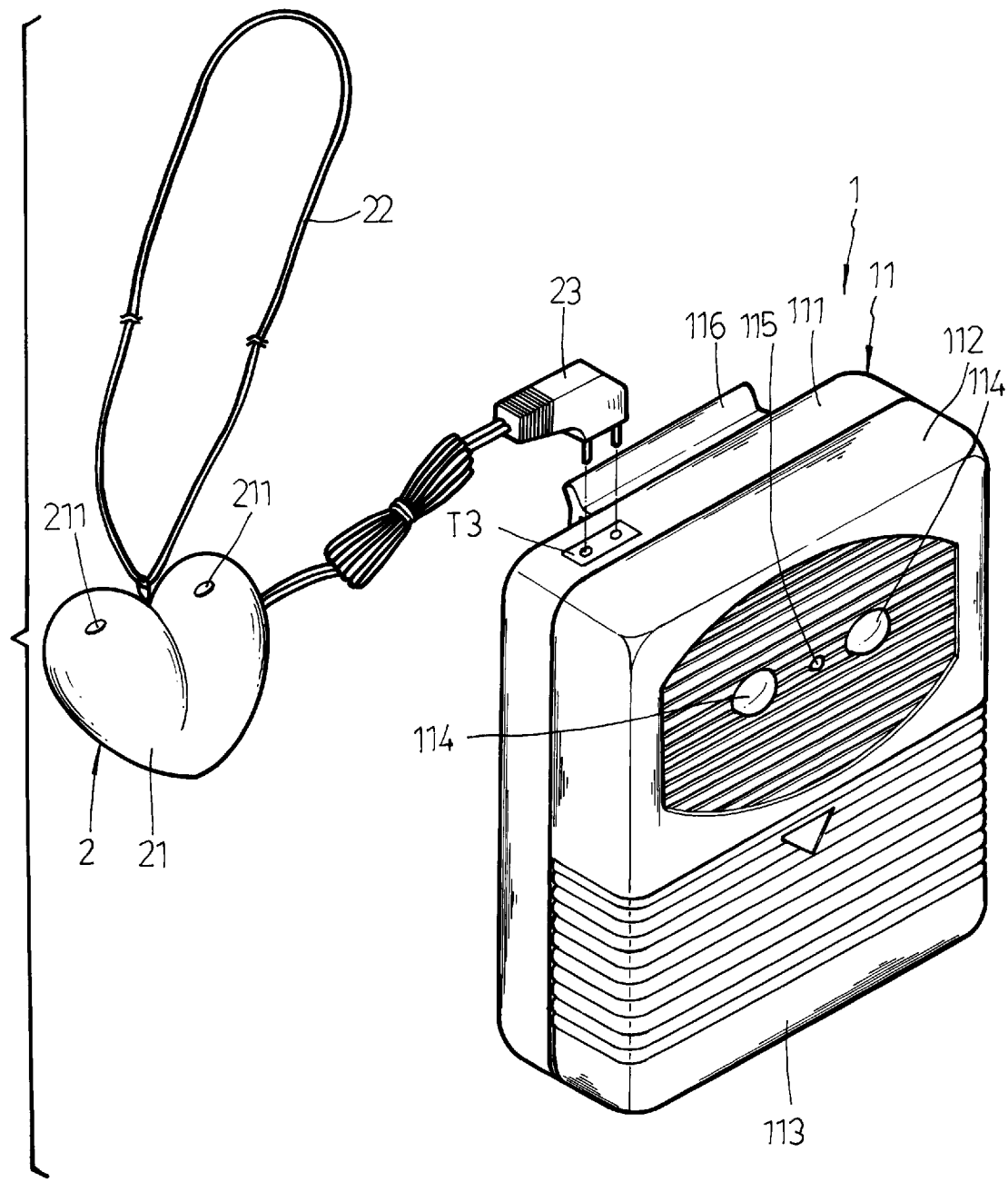
FIG. 1 is an elevational view of the outside of the present invention.
Figure 2:
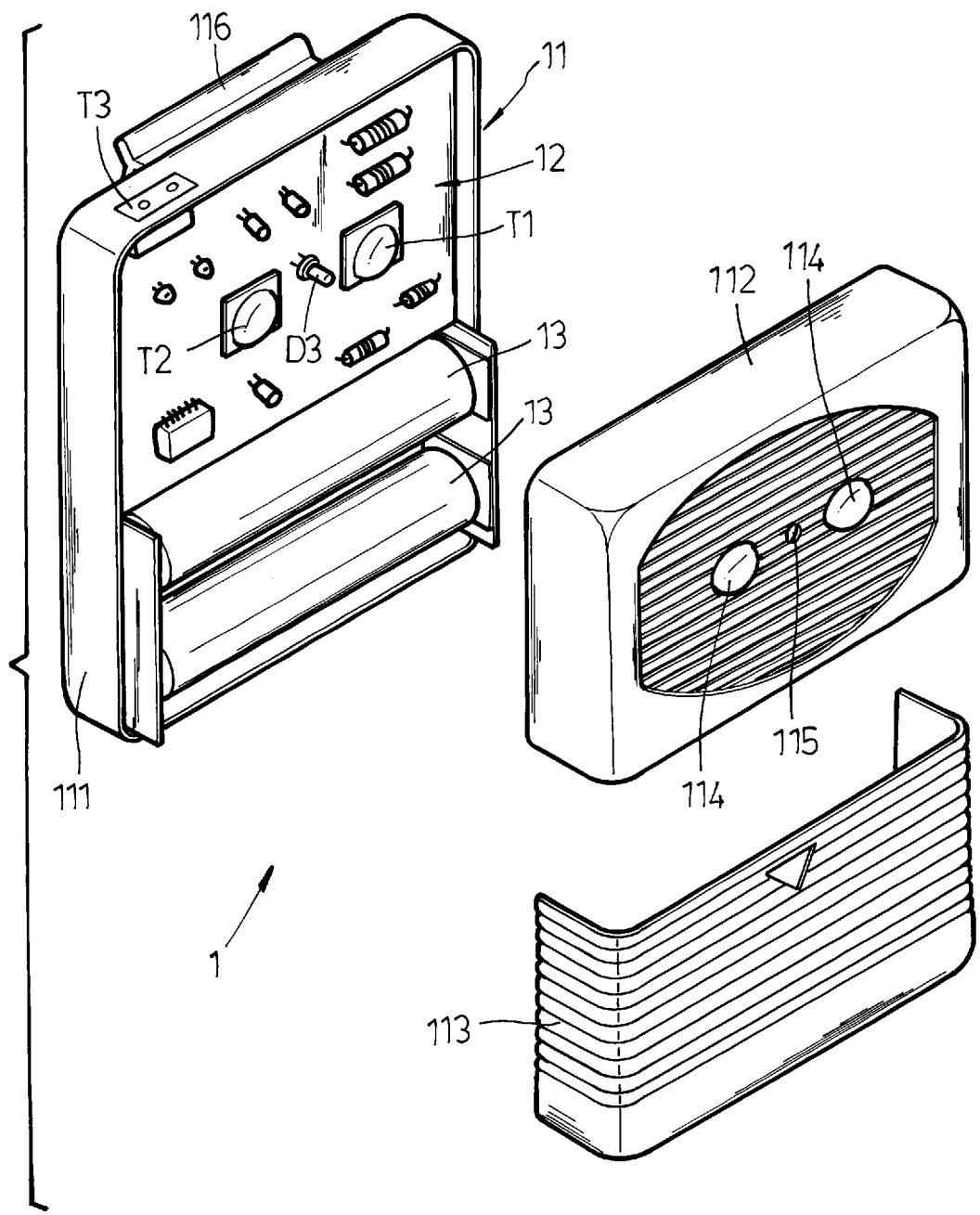
FIG. 2 is a schematic exploded view of the components of a high frequency voltage booster of the present invention.

With reference to FIGS. 1 and 2, the present invention structurally comprises a high frequency voltage booster 1 and an anion generator 2. The high frequency voltage booster 1 includes a control box body 11, a circuit board 12, and two batteries 13. The control box body 11 includes a bottom box 111, a face plate cover 112 and a battery cover 113. The bottom box 111 accommodates therein the circuit board 12 and the batteries 13, and is covered by the face plate cover 112 and the battery cover 113 respectively.

Figure 3:
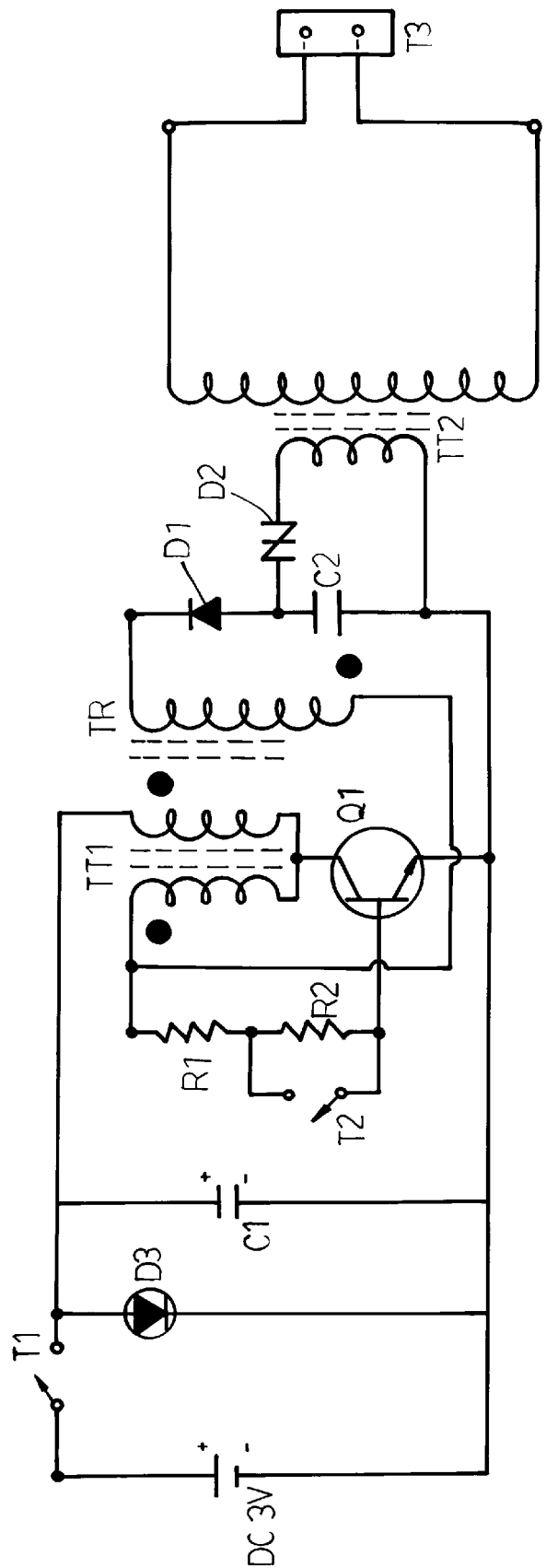
FIG. 3 is a schematic view of a high frequency high voltage circuit of the high frequency voltage booster of the present invention.

Referring to FIG. 3, the circuit board 12 has assembled thereon two touch switches T1, T2, two capacitors C1, C2, two resistors R1, R2, two transformers TT1, TT2, a transistor Q1, a thyristor TR, three diodes D1, D2, D3, and a terminal socket T3. The touch switch T1 controls supply of power from the battery 13 and may be pressed via a touch button 114 on the face plate cover 112. The battery 13 supplies 3V DC to the circuits. The capacitor C1 is used for charging until the voltage is full, and the transistor Q1 is caused to control the resistors R1, R2 to make the connection so as to form a high frequency oscillation loop, causing the entire circuit signal oscillation to become stable and therefore convertible into high frequency pulse signals. When a touch button 114 on the face plate panel 112 is pressed to contact the touch switch T2, the magnitude of the pulse signals may be changed or controlled. Transformer TT1 and thyristor TR are used to boost the voltage and cooperate with a discharge circuit formed by the diode D1, capacitor C2, and bi-directional diode D2 to cause the transformer TT2 to convert into high frequency high voltage pulse currents to be output by the terminal socket T3. The diode D3 on the high frequency voltage booster 1 may light up when the battery 13 supplies electric currents and the light is visible through a through hole 115 in the face plate cover 112 for indicating the amount of electric energy inside the battery 13.

Therefore, by providing a circuit board 12 and two batteries 13 in the high frequency voltage booster 1, a high frequency high voltage pulse current control device may be formed. Additionally, a clip or clamp 116 may be fixedly disposed at an outer rim of the control box body 11 so that the high frequency voltage booster 1 may be attached to the user's clothing for carrying around and outputting high frequency high voltage pulse currents.

Referring to FIGS. 1 and 2, the anion generator 2 is comprised of a generator body 21 accommodating therein a discharge electrode, a necklace 22 attached to the generator body 21, and a terminal connector 23. An outer rim of the generator body 21 is provided with two air vents 211 for free passage of air in and out. The generator body 21 may be hung on the necklace 22 so that it may be carried around by the user. A bottom side of the generator body 21 is connected to the terminal connector 23 so that the latter may be connected to a terminal switch T3 of the high frequency voltage booster 1 for outputting high frequency high voltage pulse currents to the discharge electrode inside the generator body 21. The discharge electrode discharges high frequency high voltage currents for generating plenty of anions. The anions may flow out through the air vents 211 to react with and decompose viruses floating in the air so as to directly purify the air around the user, thus achieving effective prevention of virus infections.

Figure 4:
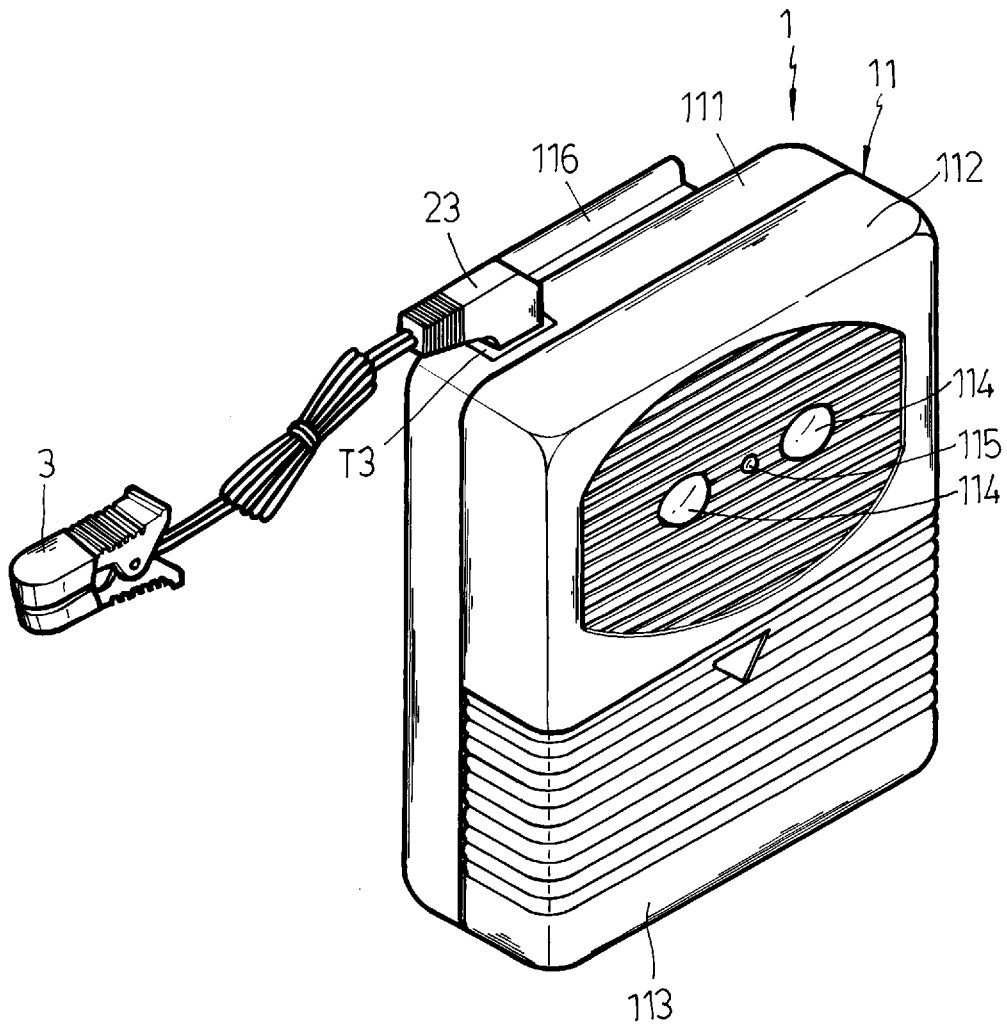
FIG. 4 is a perspective view of a preferred embodiment of an electrode clamp of the high frequency voltage booster of the present invention.
Figure 5:
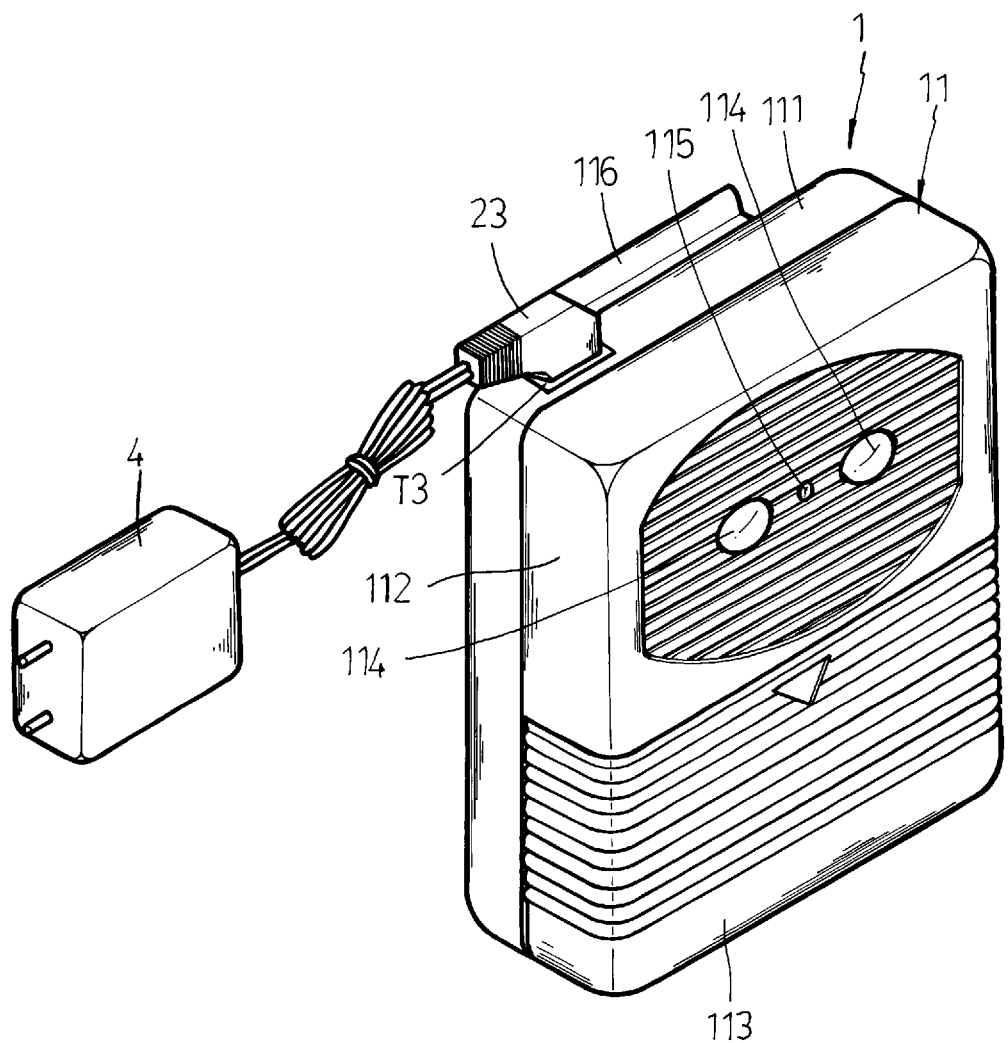
FIG. 5 is a perspective view of a preferred embodiment of a buzzer electric shock head of the high frequency voltage booster of the present invention.

The terminal socket T3 of the high frequency voltage booster 1 may transfer high frequency high voltage pulse currents. Apart from connecting the anion generator 2 to the terminal socket T3 to purify the surrounding air, an electrode clamp 3 may also be connected to the terminal socket T3 so that the high frequency high voltage pulse currents may flow to the two poles of the electrode clamp 3, as shown in FIG. 4, whereby one pole may emit magnetic wave to serve as a magnetic path while the other pole may receive the emitted magnetic wave to form a cyclic loop. The magnetic wave may be used to pierce points in the human body for stimulating blood circulation. There will also be slight electric shock at that part of the human body the electrode clamp holds, which will not only stimulate blood circulation and metabolism but also repress drowsiness. Alternatively, as shown in FIG. 5, the high frequency voltage booster 1 may be connected to a buzzer electric shock head 4, in which the switch T2 may be controlled to increase the flow of electric currents so that the terminal socket T3 may output stronger high voltage pulse currents for self defense purposes.

The above disclosure illustrates preferred embodiments of the invention only. The anion generator shown in the drawings as a heart-shaped pendant may be hung around the neck so that it may be carried around with the user, which is pleasing and practical. In fact, the appearance and shape of the anion generator may be modified to have a more pleasing shape since the discharge electrode may be disposed in its interior.

In summary, the present invention is a combination of a high frequency voltage booster and an anion generator, which utilizes the high frequency voltage booster to output high frequency high voltage pulse currents to the anion generator which will then generate many anions to react with and decompose viruses floating in the air, thereby purifying the air surrounding the user and effectively avoiding viral infections.

Although the present invention has been illustrated and described with reference to the preferred embodiment thereof, it should be understood that it is in no way limited to the details of such embodiment but is capable of numerous modifications within the scope of the appended claims.

What is claimed is:

1. A portable air purifying device, comprising:

a voltage booster, comprising a control box body, a circuit board, and at least one battery, said control box body being comprised of a bottom box, a face plate cover, and a battery cover, said bottom box accommodating therein said circuit board and said at least one battery, and being covered by said face plate cover and said battery cover respectively, an outer side of said bottom box being connected to a clip arranged to be attached to clothes on a human body; said circuit board being comprised of first and second touch switches, two capacitors, two resistors, first and second transformers, a transistor, a thyristor, three diodes, and a terminal socket assembled thereonto and connected together to form a circuit for outputting voltage pulse currents, said pulse currents having a frequency and voltage sufficiently high that when said pulses are applied to a discharge electrode, many anions are generated; an anion generator, comprising a generator body accommodating therein said discharge electrode, said first touch switch being connected between said at least one battery and said first transformer to turn said circuit on and off, said first transformer being connected to said transistor and said resistors and one of said capacitors to form an oscillator circuit, and to said second transformer, said second diode and said thyristor to form a voltage booster, a first of said two diodes and a second of said two capacitors supplying a rectified input from said battery to said capacitor, and said second switch being connected between said resistors and switchable between a relatively low voltage position and a relatively high voltage position, said resistors forming a voltage divider to vary a magnitude of said pulse signals, a necklace attached to said generator body, and a terminal connector, said generator body having two air vents for passage of air in and out of said generator body and being hung on said necklace so that it may be carried around, said terminal connector being insertable into said terminal socket of said high frequency voltage booster for outputting high frequency high voltage pulse currents to said discharge electrode inside said generator body; whereby said high frequency high voltage booster and said anion generator attachable by said necklace to the human body and by said clip to said clothes, respectively, for carrying around, and whereby when said terminal connector of said anion generator is coupled to said high frequency high voltage booster, said high frequency high voltage pulse currents cause said discharge electrode inside said generator body to generate said many anions by discharging said high frequency high voltage currents, the anions exiting through said air vents to react with and decompose viruses floating in the air to thereby purify the air around a user and effectively avoid viral infections.

2. A portable air purifying device as claimed in claim 1, wherein said terminal socket of said high frequency high voltage booster is arranged to be alternatively connected to an electrode clamp for drowsiness repression, said clamp applying a magnetic wave and mild electric shock to a body part to which it is clamped, said second switch then being switched to said relatively low voltage position.

3. A portable air purifying device as claimed in claim 1, wherein said terminal socket of said high frequency voltage booster is arranged to be alternatively connected to a buzzer electric shock head for purposes of self defense, said second switch then being switched to said relatively high voltage position.

* * * * *